United States Patent
Chon et al.

(10) Patent No.: US 9,888,866 B2
(45) Date of Patent: Feb. 13, 2018

(54) SYSTEM FOR EXTRACTING RESPIRATORY RATES FROM A PULSE OXIMETER

(75) Inventors: Ki H. Chon, Worcester, MA (US); Jinseok Lee, Worcester, MA (US)

(73) Assignee: WORCESTER POLYTECHNIC INSTITUTE, Worcester, MA (US)

( * ) Notice: Subject to any disclaimer, the term of this patent is extended or adjusted under 35 U.S.C. 154(b) by 649 days.

(21) Appl. No.: 13/823,801

(22) PCT Filed: Oct. 12, 2011

(86) PCT No.: PCT/US2011/055961
§ 371 (c)(1),
(2), (4) Date: Mar. 15, 2013

(87) PCT Pub. No.: WO2012/051295
PCT Pub. Date: Apr. 19, 2012

(65) Prior Publication Data
US 2013/0197383 A1    Aug. 1, 2013

Related U.S. Application Data

(60) Provisional application No. 61/392,271, filed on Oct. 12, 2010.

(51) Int. Cl.
*A61B 5/08* (2006.01)
*A61B 5/1455* (2006.01)
*A61B 5/00* (2006.01)

(52) U.S. Cl.
CPC ........ *A61B 5/0816* (2013.01); *A61B 5/14551* (2013.01); *A61B 5/725* (2013.01)

(58) Field of Classification Search
CPC .... A61B 5/0816; A61B 5/7267; A61B 5/0205
See application file for complete search history.

(56) References Cited

U.S. PATENT DOCUMENTS

2010/0298730 A1* 11/2010 Tarassenko .......... A61B 5/0816
600/529
2011/0301477 A1* 12/2011 Hughes ................ A61B 5/0205
600/500

FOREIGN PATENT DOCUMENTS

| WO | 2009016334 A1 | 2/2009 |
| WO | 2010030238 A1 | 3/2010 |

OTHER PUBLICATIONS

International Preliminary Report on Patentability dated Apr. 25, 2013 for PCT/US11/55961.

Chon, K.H. et al., Estimation of Respiratory Rate From Photoplethysmogram Data Using Time—Frequency Spectral IEEE Transactions on Biomedical Engineering, Aug. 2009, 2054-2063, vol. 56, No. 8.

Lu, S. et al., A New Algorithm for Linear and Nonlinear ARMA Model Parameter Estimation Using Affine Geometry, IEEE Transactions on Biomedical Engineering, Oct. 2001, 1116-1124, vol. 48, No. 10.

(Continued)

*Primary Examiner* — Etsub Berhanu
*Assistant Examiner* — Michael Catina
(74) *Attorney, Agent, or Firm* — Burns & Levinson LLP; Orlando Lopez

(57) ABSTRACT

Accurate AR method for extracting respiratory rates directly from a pulse oximeter and accurate methods of extracting respiratory rates directly from a pulse oximeter under low signal-to-noise ratio (SNR) conditions.

26 Claims, 10 Drawing Sheets

(56) References Cited

OTHER PUBLICATIONS

Xiao, X. et al., A Model Order Selection Criterion With Applications to Cardio-Respiratory-Renal Systems, IEEE Transactions on Biomedical Engineering, Mar. 2005, 445-453, vol. 52, No. 3.

Zou, R. et al., Robust Algorithm for Estimation of Time-Varying Transfer Functions IEEE Transactions on Biomedical Engineering, Feb. 2004, 219-228, vol. 51, No. 2.

Lee, J. et al., Respiratory rate extraction via an autoregressive model using the optimal parameter search criterion. Annuals of Biomedical Engineering, 38(10), Oct. 2010: 3218-3225.

International Search Report and Written Opinion dated May 29, 2012 for PCT/US11/55961.

* cited by examiner

Form an initial set of particles, $R^j(0)$, $i=1,...I$, and give them uniform weights $w^j(0) = 1/I$.

1. Predict the new set of particles $R^j(n)$ by propagating the resampled set $\bar{R}^j(n-n_{sam})$ 2. Obtain measurement $P(n)$ by the OPS model in the region of interest.

3. Evaluate each particle weight $w^j(n)$ according to likelihood functions $p(P(n)|R^j(n))$ 4. Compute the respiratory state (rate) $R(n)$ as the weighted sum of particles $E[R^j(n)]=\Sigma^I_{i=1} w^j(n)R^j(n)$ 5. Resample the particles, $\bar{R}^j(n)$

FIG. 4

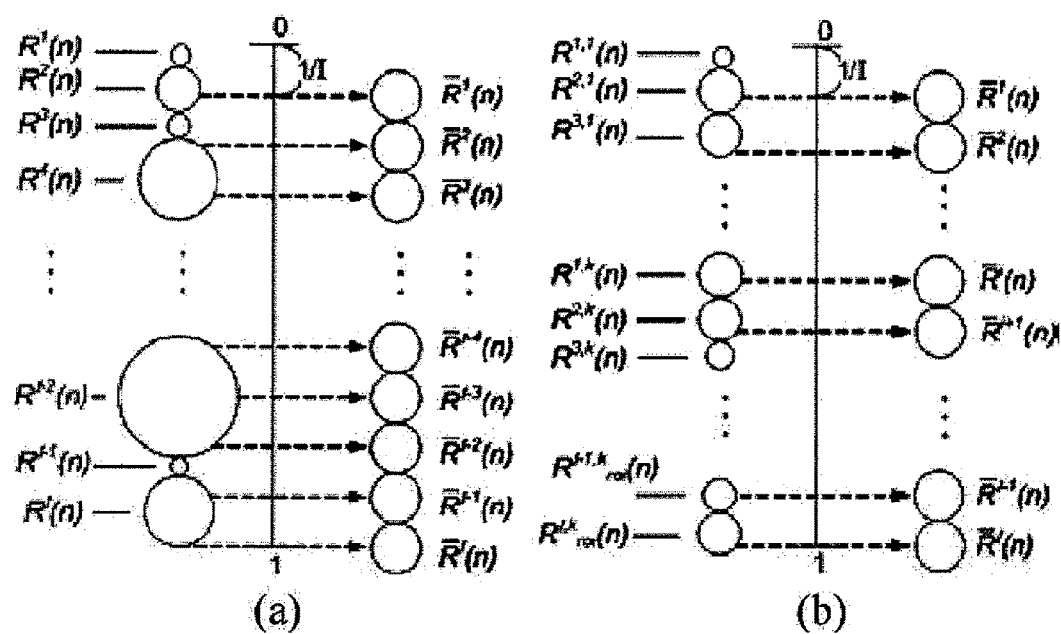
FIGS. 5a-b

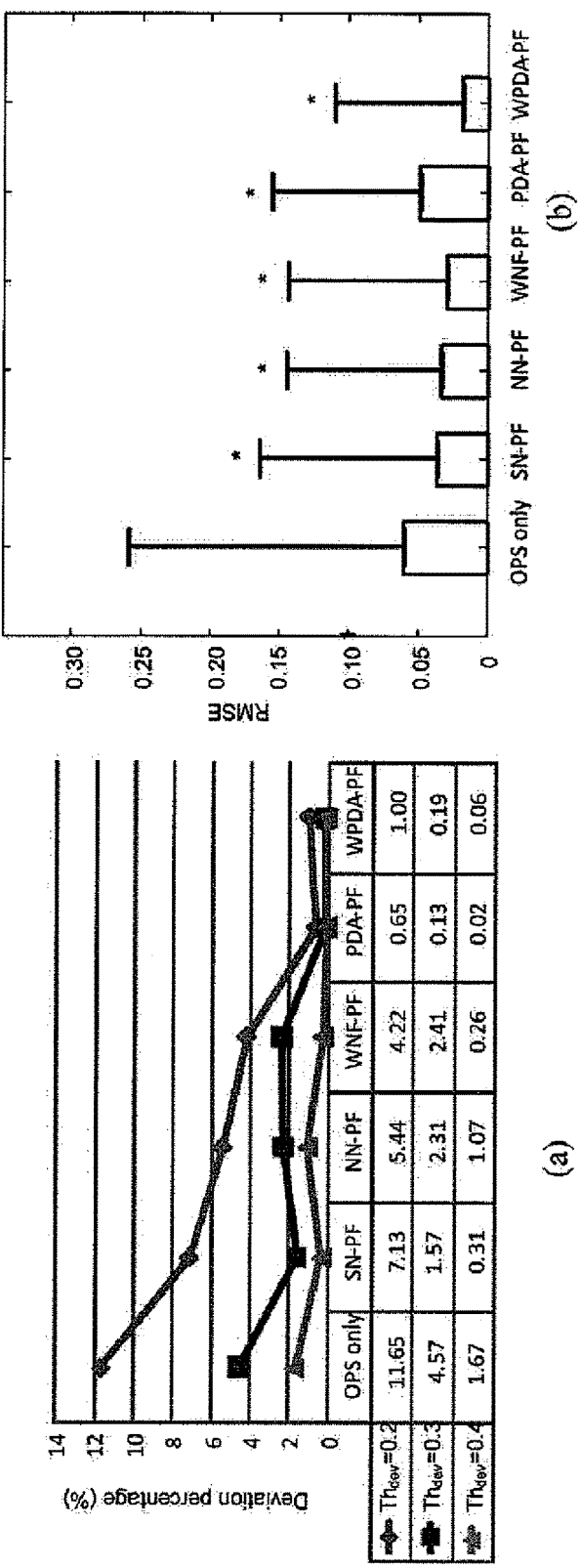
FIGS. 6a-b

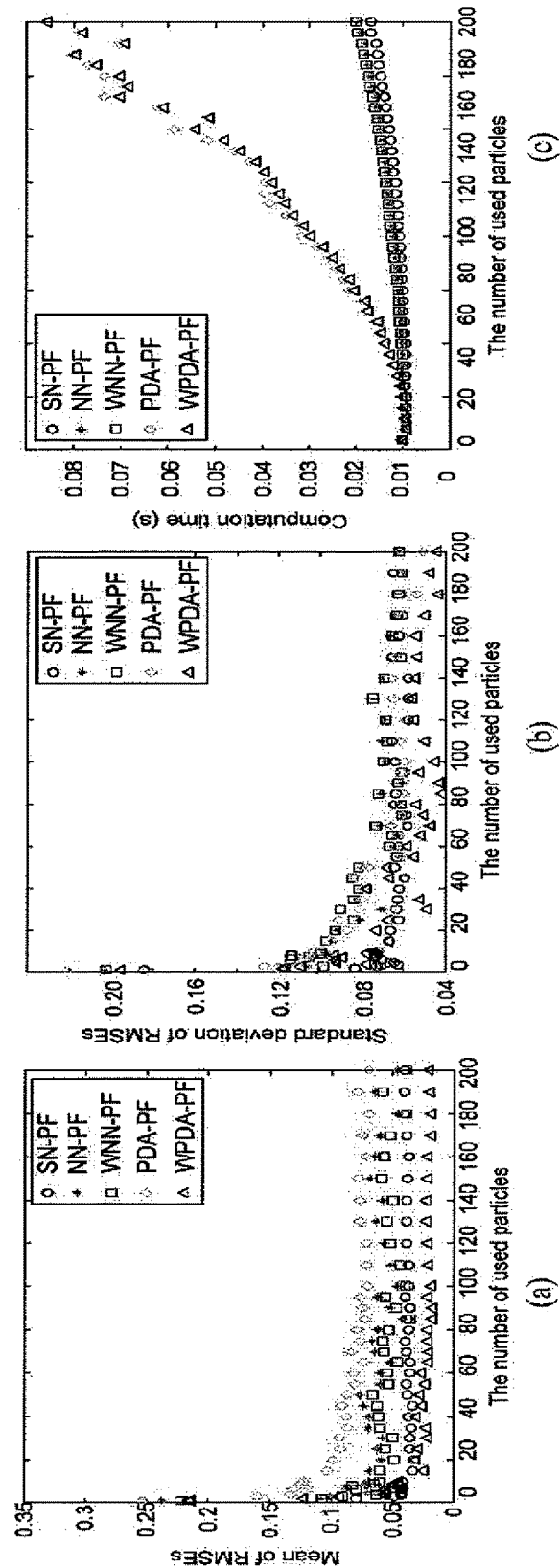
FIGS. 7a-c

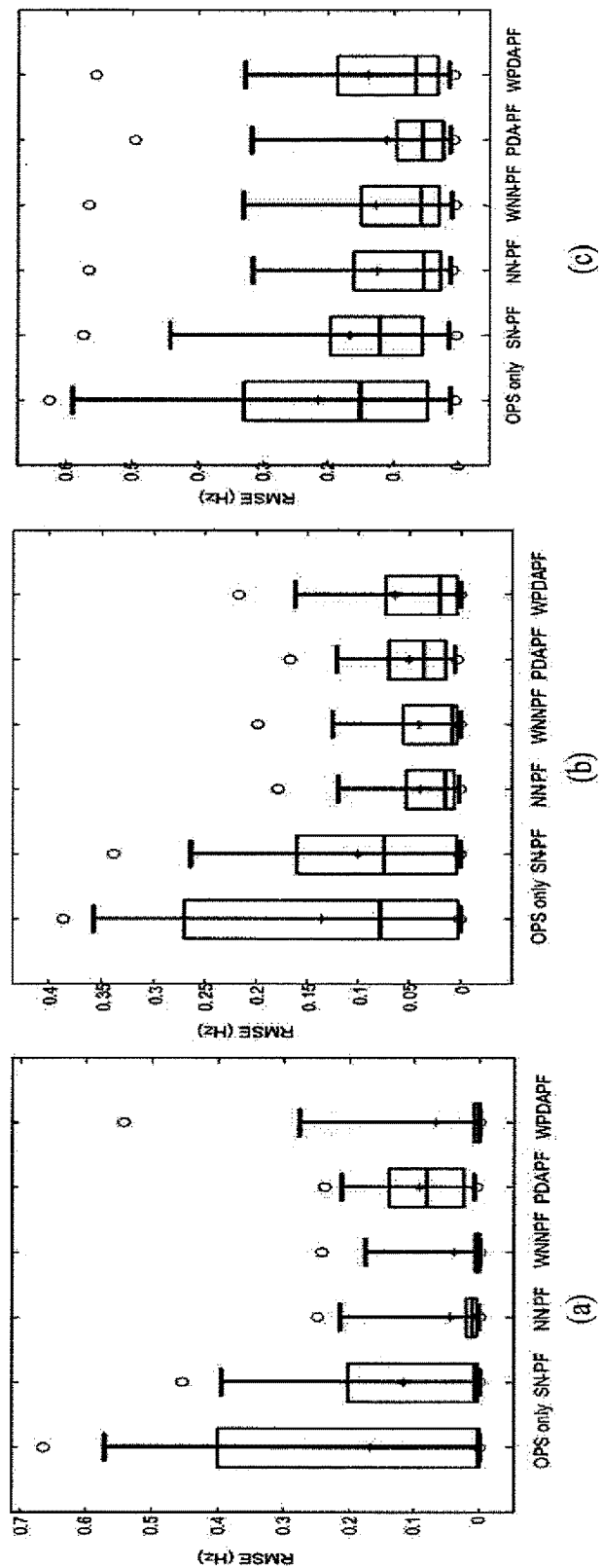
FIGS. 8a-c

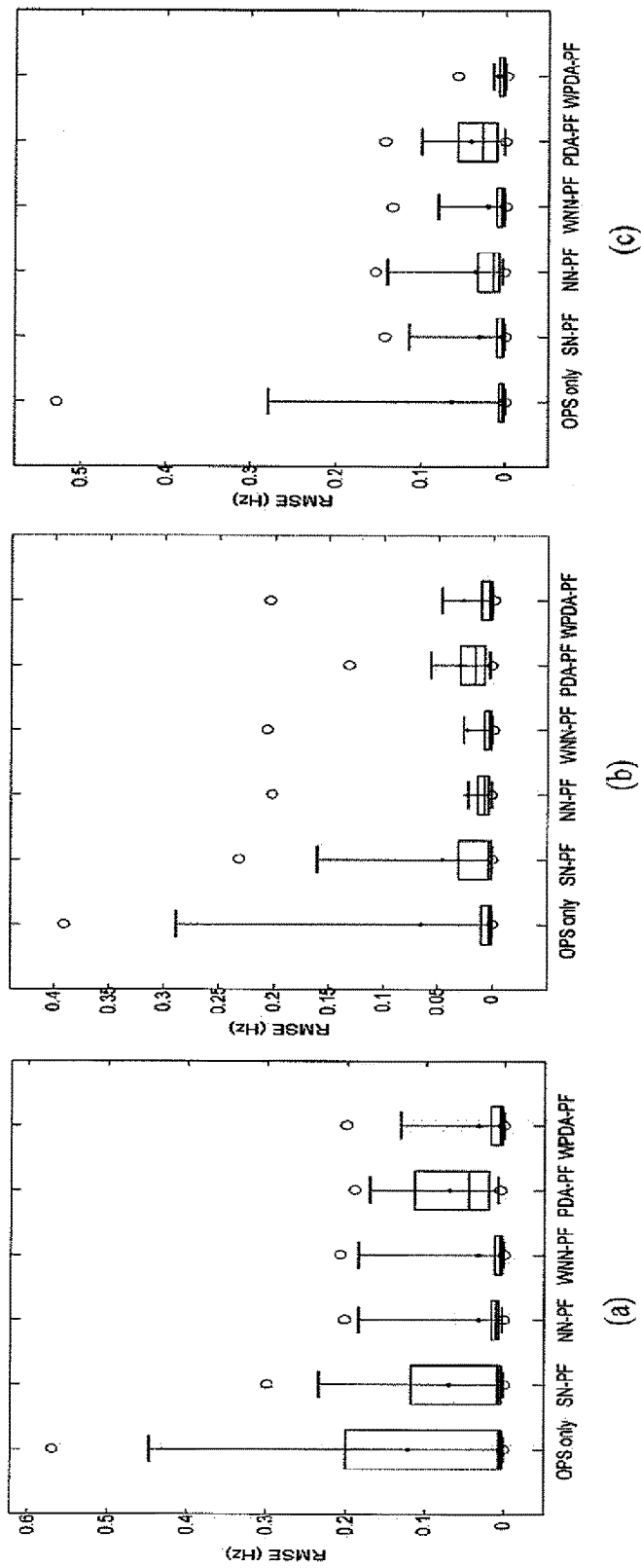
FIGS. 9a-c

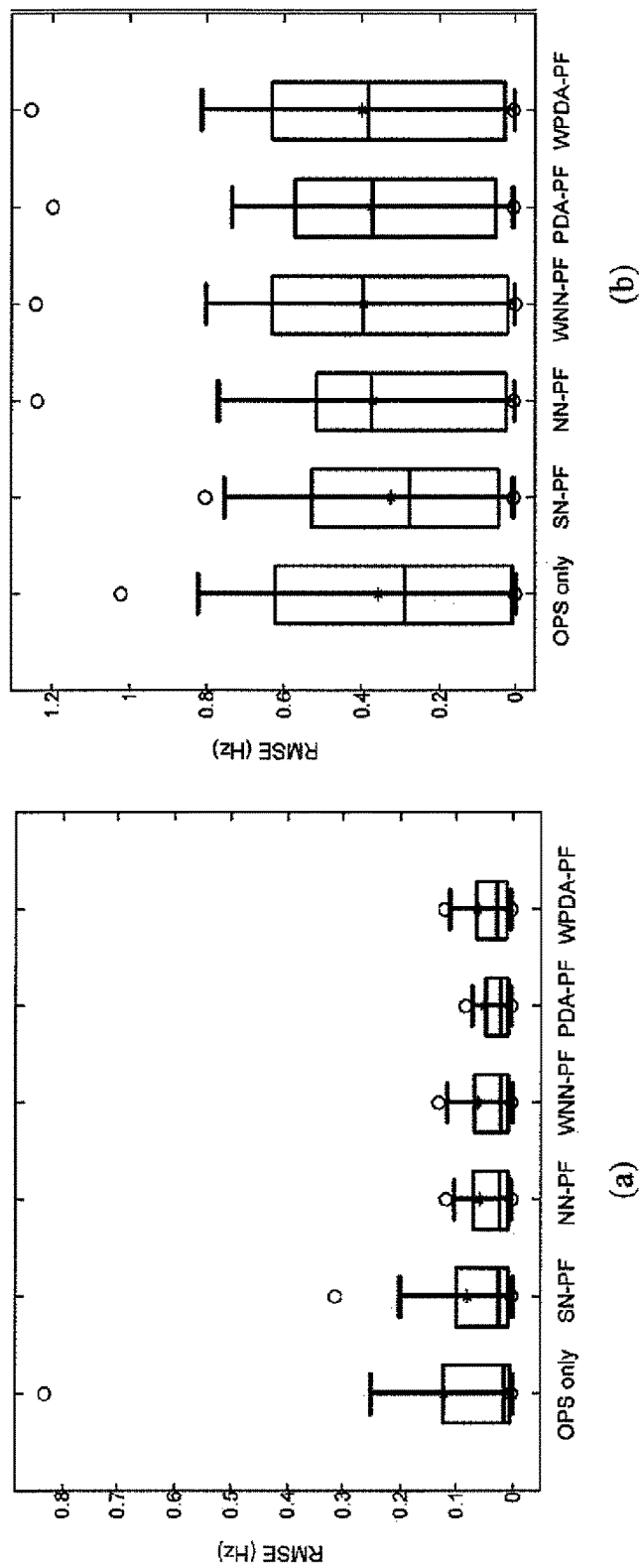
FIGS. 10a-b

SYSTEM FOR EXTRACTING RESPIRATORY RATES FROM A PULSE OXIMETER

CROSS-REFERENCE TO RELATED APPLICATIONS

This application is a U.S. national stage application under 35 U.S.C. 371 of co-pending International Application No. PCT/US11/55961 filed on Oct. 12, 2011 and entitled SYSTEM FOR EXTRACTING RESPIRATORY RATES FROM A PULSE OXIMETER, which in turn claims priority to U.S. Provisional Patent Application No. 61/392,271 filed on Oct. 12, 2010, both of which are incorporated by reference herein in their entirety for all purposes.

STATEMENT REGARDING FEDERALLY SPONSORED RESEARCH OR DEVELOPMENT

This work was funded in part by the Office of Naval Research, Work Unit N00014-08-1-0244. The U.S. Government has certain rights in the invention.

BACKGROUND

Respiratory rate is one of the important vital signs, and much effort has been centered on extracting it from pulse oximeter and electrocardiogram recordings. The research has been driven largely by the desire to reduce the number of sensors that need to be connected to a patient to obtain vital signs.

Recent promising approaches based on time-frequency spectral techniques have been used to extract respiratory rates directly from a pulse oximeter. With recognition that respiration modulates heart rate and that they are both time-varying, time-frequency analyses were used to extract the former signal. Specifically, the continuous wavelet transform (CWT) and variable frequency complex demodulation (VFCDM) methods were utilized to extract either frequency modulation or amplitude modulation seen in the frequency range associated to the heart rate. Both CWT and VFCDM methods have been shown to provide accurate respiratory rate extraction in the low- and moderate-breathing rates (12-36 breaths/min). However, these time-frequency methods' capability became less reliable with increased respiratory rates.

In a recent work, it has been shown that the high resolution time-frequency analysis of the pulse oximeter signal followed by taking the power spectrum of the extracted frequency modulation signal around the heart rate frequency resulted in the best accuracy among all compared methods, including the time-invariant autoregressive (AR) method. While the AR method was not as accurate as the time-frequency methods, it has many attractive features because it is more computationally efficient and works reasonably well even with short data records. It has been conjectured that one of the key reasons the AR method did not perform as well as other methods was due to an inefficient model order search criterion, namely, its reliance on the Akaike information criterion (AIC). Further, an arbitrary decision regarding the proper choice of the poles and the phase related to the estimated AR coefficients had to be made in order to extract the correct respiratory rate, which can also compromise its accuracy.

There is a need for a more accurate AR method for extracting respiratory rates directly from a pulse oximeter. Even with a more accurate AR method for extracting respiratory rates directly from a pulse oximeter, as the Signal-to-Noise Ratio (SNR) decreases, the accuracy of the method will be affected. There is a need for an AR based method for extracting respiratory rates directly from a pulse oximeter that produce accurate results at low SNR.

BRIEF SUMMARY

Embodiments of more accurate AR method for extracting respiratory rates directly from a pulse oximeter and of accurate methods of extracting respiratory rates directly from a pulse oximeter under low signal-to-noise ratio (SNR) conditions are disclosed herein below.

In one embodiment, an autoregressive (AR) model method, using a projection onto linearly independent non-orthogonal bases, by means, in one instance, of the optimal parameter search (OPS) technique, provides accurate respiratory rate extraction especially for high-breathing rates (36-48 breaths/min). The AR method includes obtaining parameters for an autoregressive (AR) representation using a projection onto linearly independent non-orthogonal bases and factorizing the estimated AR parameters into multiple pole terms. The pole with the highest magnitude is chosen to represent a respiratory rate.

In another embodiment, a sequential Monte Carlo method, referred to as particle filtering (PF), where a distribution of respiratory rate is the distribution approximated by Monte Carlo sampling, measurements are magnitudes and phase of poles for a frequency transfer function of the AR representation, the magnitudes and phase of the poles obtained by using a projection onto linearly independent non-orthogonal bases as disclosed above. The PF method has gained much recognition in recent years and has mainly been used for tracking moving targets. Recently, much effort has centered on developing efficient PF algorithms for real-time implementation.

These teachings formulate a general framework for respiratory extraction based on the PF algorithm combined with OPS. In one instance, five different likelihood functions are used for estimating the probability density function. These five different likelihood functions were examined to determine which among the five provided the best results for varying levels of SNR and breathing rates. The efficacy of the PF-OPS embodiment this examined by comparing it to the OPS-based AR model without PF, using pulse oximeter recordings from 33 healthy human subjects breathing at 12, 18, 24, 30, 36, 42, 48, 60, 72, and 90 breaths/min.

Embodiments of systems and computer program product that implement the method of these teachings are also disclosed.

For a better understanding of the present teachings, together with other and further needs thereof, reference is made to the accompanying drawings and detailed description and its scope will be pointed out in the appended claims.

BRIEF DESCRIPTION OF THE DRAWINGS

FIG. 4 is representation of PF algorithm for respiratory rate extraction;

FIGS. 5A-5B show ilustrations of resampling processes;

FIGS. 6A-B show results of one-hundred simulations were performed in order to estimate the respiratory rate;

FIGS. 7A-C show Mean, standard deviation, and computation time of the average of 100 realizations according to the number of particles used from 1 to 200;

FIGS. 8A-C show RMSEs in the respiratory range of LF (0.2-0.3 Hz), HF (0.4-0.6), and UHF (0.7-0.8) for the supine position;

FIGS. 9A-C are RMSEs in the respiratory range of LF (0.2-0.3 Hz), HF (0.4-0.6), and UHF (0.7-0.8) for the upright position; and FIGS. 10A-B are RMSEs in the respiratory range of EHF (1.0-1.5 Hz) for the upright position.

DETAILED DESCRIPTION

Figure 1:
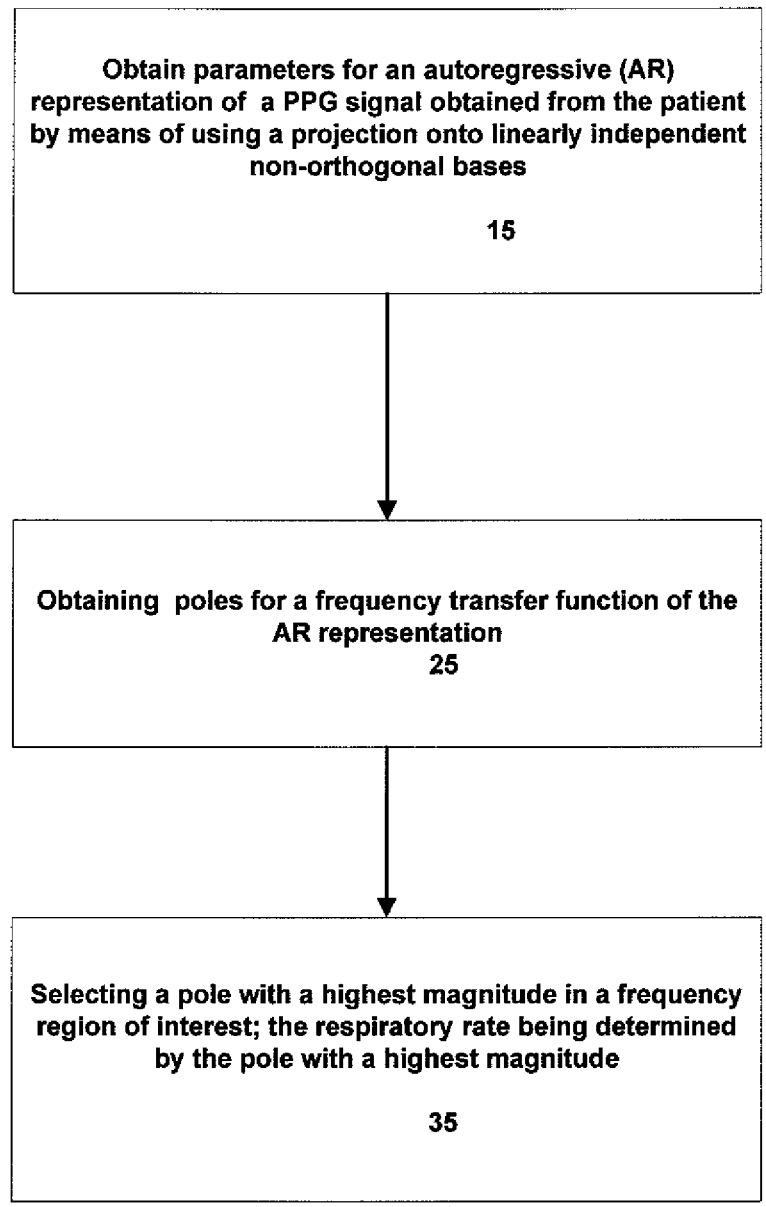
FIG. 1 is a schematic flowchart representation of one embodiment of the method of these teachings.

The following detailed description is of the best currently contemplated modes of carrying out these teachings. The description is not to be taken in a limiting sense, but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

To assist in the understanding of the present teachings the following definitions are presented.

A "likelihood function," as used herein, is the probability of obtaining observed outcomes for given parameter values.

"Recursive Bayesian estimation," as used herein, is a approach, using probabilities, for estimating a probability density function recursively over time.

A "Monte Carlo" method, as used herein, is a method that uses repeated random sampling to compute results. Monte Carlo sampling can be described as approximating a probability distribution by a discrete distribution where the distribution is known at a finite number of samples of the independent variable.

"Particles," as used herein, identifies the finite number of samples of the independent variable at which the discrete distribution is known.

"Weights," as used herein in regards to "particles," refers to the value of the discrete distribution at each of the "particles."

"Sequential Monte Carlo" methods, as used herein, are methods that estimate the probability distribution(s) by propagating "particles" according to a system model(s). "Sequential Monte Carlo" method and also referred to as bootstrap filtering, the condensation algorithm, particle filtering, interacting particle approximations and survival of the fittest methods. Hereinafter, "Sequential Monte Carlo" methods are referred to as Monte Carlo Particle Filtering methods or simply as Monte Carlo Particle Filtering. It should be noted that the use of the term Monte Carlo Particle Filtering is not meant to be limiting and that the variants and differently named "Sequential Monte Carlo" methods are all within the scope of these teachings. "Sequential Monte Carlo" method/Monte Carlo Particle Filtering methods are described in M. S. Amlampalam, S. Maskell, N. Gordon, and T. Clapp, "A tutorial on particle filters for online nonlinear/non-Gaussian Bayesian tracking," *IEEE Trans. Signal Process.*, vol. 50, no. 2, pp. 174-188, February 2002, U.S. Patent Publication No. 20100274102, corresponding to the U.S. patent application Ser. No. 12/640,278, filed on Dec. 17, 2009, U.S. Pat. No. 7,391,906 to Blake, issued Jun. 24, 2008, and U.S. Pat. No. 6,882,959 to Rui et al., issued on Apr. 19, 2005, all of which are Incorporated by reference herein in their entirety for all purposes.

In one embodiment, shown in FIG. 1, the method of these teachings includes obtaining parameters for an autoregressive (AR) representation of a photoplethysmography (PPG) signal obtained from the patient, the parameters being obtained using projection onto linearly independent non-orthogonal bases (15, FIG. 1), obtaining poles for a frequency transfer function of the AR representation (25, FIG. 1) and selecting a pole with a highest magnitude in a frequency region of interest, the respiratory rate being determined by the pole with a highest magnitude (35, FIG. 1).

In one instance, in the above disclosed embodiment of the method of these teachings, the frequency region of interest is between about 0.15 Hz and about 0.9 Hz. In another instance, the frequency region of interest is between about 0.15 Hz and about 1.5 Hz.

The above disclosed embodiment of the method of these teachings can also include filtering the PPG signal before obtaining parameters for the AR representation and downsampling the filtered PPG signal.

In another embodiment of the method of these teachings, the method includes obtaining, from an autoregressive (AR) representation of a photoplethysmography (PPG) signal obtained from the patient, the respiratory rate of the patient using an iterative Particle Filtering Monte Carlo method, where a distribution of respiratory rate is the distribution approximated by Monte Carlo sampling, measurements are magnitudes and phase of poles for a frequency transfer function of the AR representation, the magnitudes and phase of the poles obtained are shown in steps 15 and 25 of FIG. 1.

In one instance, in the above described embodiment, the iterative Particle Filtering Monte Carlo method includes:
  selecting an initial group of particles, each particle from said initial group being a different value for the respiratory rate; each particle from said initial group being assigned a weight equal to an inverse of a number of particles said initial group;
  obtaining a new group of particles by propagating the initial group of particles;
  obtaining measurements; measurements being magnitudes and phase of poles for the frequency transfer function of the AR representation obtained by:
    obtaining parameters for the AR representation using a projection onto linearly independent non-orthogonal bases;
    obtaining the poles for a frequency transfer function of the AR representation;
  obtaining a new weight for each particle from said new group by using a predetermined likelihood function;
  select a candidate respiratory rate of a patient equal to a weighted sum of the particles in the new group of particles; and
  resampling the new group of particles, as shown in FIG. 4.

In different instances of the above described embodiment, the likelihood function (also referred to as the likelihood) is the strongest neighbor (SN) likelihood, the nearest neighbor (NN) likelihood, the weighted nearest neighbor (WNN) likelihood, the probability data association (PDA) likelihood, or the weighted probability data association (WPDA) likelihood.

In one instance of the above described embodiment that uses an iterative Particle Filtering Monte Carlo method, a frequency region of interest is between about 0.15 Hz and about 1.5 Hz.

Figure 2:
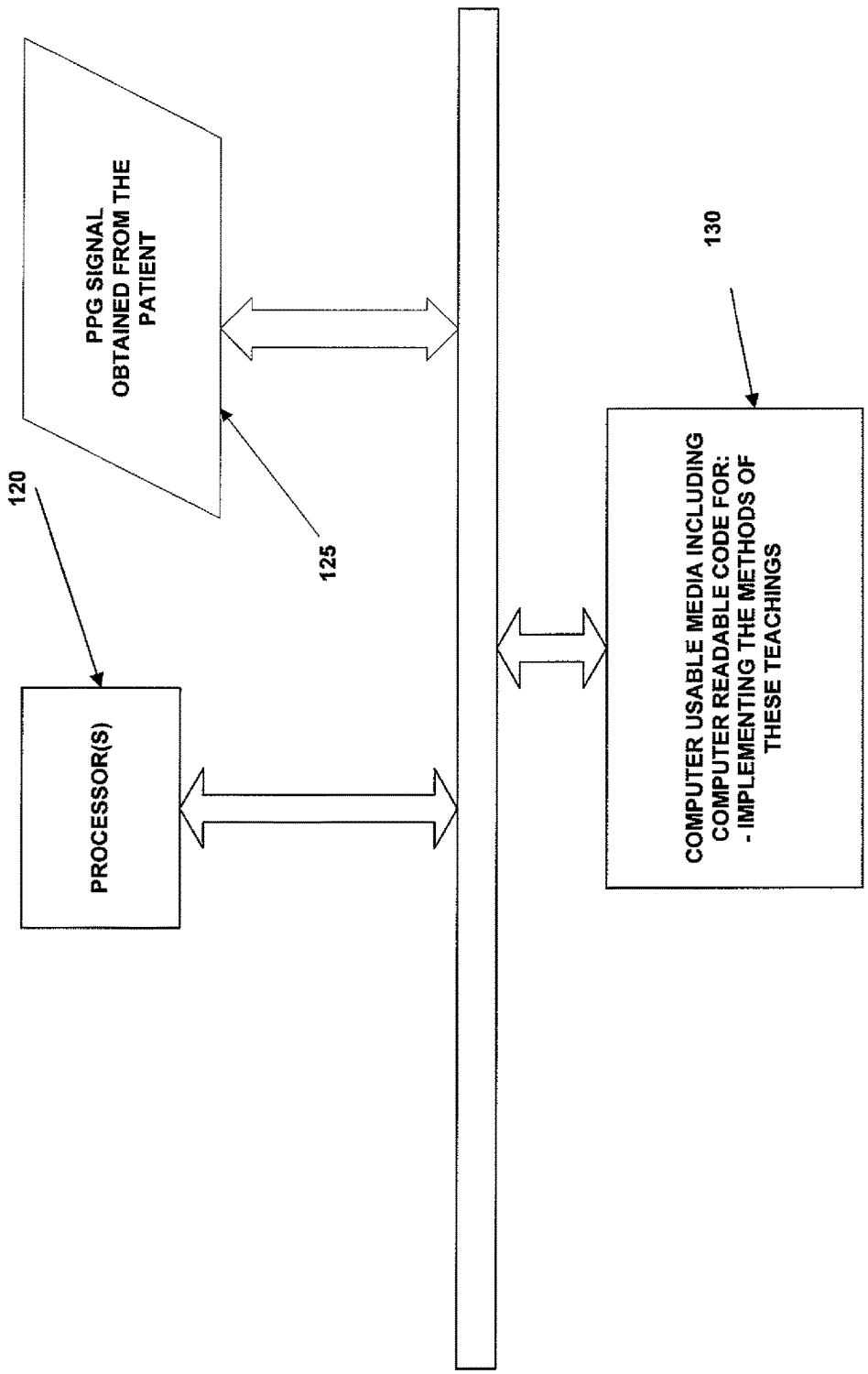
FIG. 2 is a schematic block diagram representation of one embodiment of the system of these teachings.

In one embodiment of the system of these teachings, shown in FIG. 2, the system includes one or more processors 120 and one or more computer usable media 130 that has computer readable code embodied therein, the computer readable code causing the one or more processors to execute at least a portion of the method of these teachings. The system also receives the PPG signal obtained from the patient 125. The one or more processors 120, the one or more computer usable media 130 and the data from the PPG signal are operatively connected.

In one instance, in the embodiment obtaining respiratory rate from an AR model by means of projection onto linearly independent non-orthogonal bases, the one or more computer usable media 130 has computer readable code embodied therein that causes the one or more processors 120 to obtain parameters for an autoregressive (AR) representation of a PPG signal obtained from the patient, the parameters being obtained using projection onto linearly independent non-orthogonal bases, obtain poles for a frequency transfer function of the AR representation and select a pole with a highest magnitude in a frequency region of interest, a respiratory rate being determined by the pole with a highest magnitude.

In another instance, in the embodiment obtaining respiratory rate using an iterative Particle Filtering Monte Carlo method, the one or more computer usable media 130 has computer readable code embodied therein that causes the one or more processors 120 to obtain, from an autoregressive (AR) representation of a photoplethysmography (PPG) signal obtained from the patient, the respiratory rate of the patient using an iterative Particle Filtering Monte Carlo method, where a distribution of respiratory rate is the distribution approximated by Monte Carlo sampling, measurements are magnitudes and phase of poles for a frequency transfer function of the AR representation, the magnitudes and phase of the poles obtained by obtaining parameters for the AR representation using a projection onto linearly independent non-orthogonal bases and obtaining the poles for a frequency transfer function of the AR representation.

Details of and results from several embodiments of the method of these teachings are disclosed hereinbelow. It should be noted that these detail embodiment are not limiting of these teachings.

A. Respiratory Rate Extraction with AR Model

Respiratory rates are formulated as an autoregressive (AR) model $$x(n) = -\sum_{k=1}^{K} a_k x(n-k) + e(n) \quad (1)$$

where K is the model order, $a_k$ are the unknown coefficients, and e(n) is the prediction error. A projection onto linearly independent non-orthogonal bases, by means, in one instance, of the OPS, is used to obtain accurate parameter estimation among the overdetermined model order K. The OPS can be designed to automatically select the optimal model order for any signal, thus, can be tuned to each signal without any human subjectivity. With any initial model order of K, the significant model order $K_{opt}$ is determined by the ratio of two neighboring projection distances. Once the unknown AR parameters $a_k$ are estimated, they are formulated as the transfer function H(z) as follows:

$$H(z) = \frac{1}{\sum_{k=1}^{K_{ops}} a_k z^{-k}} = \frac{z^{K_{ops}}}{(z-z_1)(z-z_2)\ldots(z-z_{K_{ops}})} \quad (2)$$

where the AR coefficients are factorized into $K_{ops}$ pole terms, where $K_{ops} \leq K$. The real and complex conjugate poles define the power spectral peaks with the larger magnitude poles corresponding to the greater magnitudes. The resonant frequency of each spectral peak is given by the phase angle of the corresponding pole; the phase angle θ of a pole at frequency f is defined as 2πfΔt, where Δt is the sampling interval. Among the poles, the region of interest (ROI) for respiratory rates is set between $f_{low}$, and $f_{high}$ (e.g., but not limited to, about 0.15 and about 1.5 Hz in one instance or about 0.15 Hz and about 0.9 Hz in another instance). The number of the pole angles within the ROI is denoted by $K_{roi}$. If $K_{roi} \geq 2$, the pole with the highest magnitude is chosen to be representative of the respiratory rate.

The OPS method overcomes the main limitations of the previously used methods, such as AIC and MDL. In addition, the OPS can be designed to automatically select the optimal model order for any signal, thus, can be tuned to each signal without any human subjectivity.

Details regarding the OPS are disclosed in Lu, S., K. H. Ju and K. H. Chon. A new algorithm for linear and nonlinear ARMA model parameter estimation using affine geometry. *IEEE Trans Biomed Eng* 48(10):1116-24 2001, incorporated by reference herein is entirety and for all purposes, thus the OPS is only briefly summarized below. With an initial model order selection of $p_{ini}$, the OPS algorithm is designed to select only the linearly-independent vectors from the pool of candidate vectors. For Eq. (1) with the selected model order of $p_{ini}$, the candidate vectors are the following: x(n-1), . . . , x(n-$P_{ini}$). These candidate vectors can be arranged as the matrix shown in Eq. (3), where N is the total number of data points.

$$\begin{matrix} x(0) & x(-1) & \ldots & x(1-p_{ini}) \\ x(1) & x(0) & \ldots & x(2-p_{ini}) \\ \vdots & \vdots & \ldots & \vdots \\ x(n-1) & x(n-2) & \ldots & x(n-p_{ini}) \\ \vdots & \vdots & \ldots & \vdots \\ x(N-1) & x(N-2) & \ldots & x(N-p_{ini}) \end{matrix} \quad (3)$$

The first step toward achieving linear independence among candidate vectors is to select x(n-1) as the first candidate vector. The next candidate vector x(n-2), and the first candidate vector x(n-1), are then used to determine linear independence by using x(n-1) to fit x(n-2) using the least squares method and calculating the error between x(n-2) and the estimated vector. Once it has been determined that x(n-2) is a linear independent candidate vector, the vectors x(n-1) and x(n-2) are used to estimate the candidacy of the linear independence of x(n-3). This procedure is continued until all the linearly independent vectors are selected to form a new candidate vector pool. With the new candidate pool of R linearly independent vectors, least-squares analysis is performed on the following equation:

$$x(n) = \theta_m^T \emptyset + e(n), \quad (4)$$

where $$\theta_m = [g_0, g_1, \ldots, g_R]^T, \text{ and } \emptyset = [w_0, w_1, \ldots, w_R].$$

To minimize the error in Eq. (4), the cost function in Eq. (5) is used and parameter estimates can be according to Eq. (6)

$$I_N(\theta_m) = [x(n) - \theta_m^T \emptyset]^2. \quad (5)$$

$$\overline{\theta}_m = [\emptyset \emptyset^T]^{-1} \emptyset x(n). \quad (6)$$

The projection distance is calculated as:

$$c_m = \frac{1}{N} \sum_{n=1}^{N} \hat{\theta}_m^2 w_m(n)^2, \quad (7)$$

$$m = 1, \ldots R.$$

With an initial model order of $p_{ini}$, the significant model order $p_{opt}$ is determined by the ratio of two neighboring projection distances described as:

$$p_{opt} = \arg\max_{m \in \{1, \ldots, p_{ini}\}} \left( \frac{c_{m-1} - c_m}{c_m} \cdot 100 \geq \tau_{th} \right), \quad (8)$$

where $c_m$ is the $m^{th}$ longest projection distance and $\tau_{th}$, is a threshold percentage. It has been shown in Zou, R., H. Wang and K. H. Chon. A robust time-varying identification algorithm using basis functions. *Ann Biomed Eng* 31(7):840-53 2003, which is Incorporated by reference herein in its entirety for all purposes, that a $\tau_{th}$ value of 25 works well in most cases.

In one instance, the AR model respiratory rate extraction approach disclosed hereinabove includes pre-filtering of the PPG waveforms in order to minimize the cardiac effects. In one instance, the PPG waveforms are detrended, filtered and downsampled to 2 Hz so that the angular resolution can be increased between 0 and 1 Hz.

In previous studies, the OPS showed better performance than both CWT and VFCDM-based time-frequency spectral techniques for high respiratory rates (higher than 0.6 Hz) but not at lower breathing rates (0.2-0.6 Hz). The main advantage of the OPS was found to be that the computational speed was approximately five times faster than VFCDM and 30 times faster than CWT. In addition, the OPS, because it is an AR-model-based method, can perform reliable respiratory rate estimation using only half of the data required by either the CWT or VFCDM methods.

The accuracy of the autoregressive (AR) model method disclosed herein above should be aided by the OPS as it has been shown to be more accurate than the well-known model order criteria such as Akaike information criterion, minimum description length, and the fast orthogonal search criterion. However, as the SNR decreases, the probability increases that incorrect poles are associated with the highest magnitude, which ultimately affects the accuracy of the method.

TABLE I

FALSE DETECTION OF 0.6070 WITH −10 dB SNR: ANGLES AND MAGNITUDES OF CANDIDATE POLES AT TIME 60 S IN FIG. 1(b)

| Angle | 0.6070 | 0.6066 | 0.4022 | 0.3997 | 0.2403 |
|---|---|---|---|---|---|
| Magnitude | 0.9887 | 0.1929 | 0.8003 | 0.9852 | 0.9433 |

Figure 3:
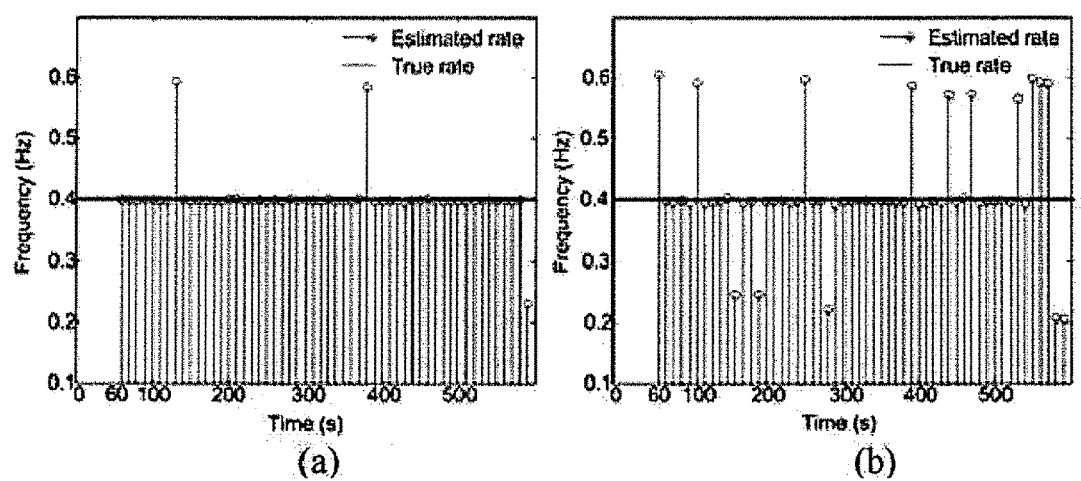
FIG. 3 is a schematic graphical representation of a test signal using one embodiment of the method of these teachings.

The aim of the study was to improve the accuracy of an AR model approach compared to the time-frequency methods for lower breathing rates and to extend capability to extract respiratory rates as high as 90 breaths/min. To illustrate the limitation of the OPS-model-based respiratory rate extraction, a simple simulation example is provided to show how and when the method succumbs to noise perturbation. The test signal involves two frequencies chosen so that they represent the frequency responses of the heart rate and the normal respiratory rate, as shown shortly:

$$y(n) = A_h \cos\left(2\pi f_h(n) \frac{n}{f_s} + \phi_h\right) + A_b \cos\left(2\pi f_b(n) \frac{n}{f_s} + \phi_b\right) + N_e \quad (9)$$

where $f_h(n)$ and $f_b(n)$ are the heart rate and respiratory rate, respectively. Øh and Øb are phases associated to the heart rate and respiratory rates, respectively, and $f_s$ is the sampling rate. For the simulation example, $A_h$ and $A_b$ were set to 10 and 1, respectively. The $f_h(n)$ and $f_b(n)$ were set to 2.0 and 0.4 Hz, respectively, and Øh and Øb were randomly generated between 0 and $2\pi$ with uniform distribution. In addition, the signal was corrupted with two different levels of Gaussian white noise (GWN) $N_e$ so that the SNR are −5 and −10 dB. 60 000 samples were generated for both SNR with a sampling rate of 100 Hz, which resulted in 10 min of data. The respiratory rate estimation was performed on 60-s segment waveforms of the test signal, and the waveform segment was shifted by 10-s for the entire 10-min duration. Thus, each 60-s segment waveform had a 50-s overlap, and 55 segments were obtained for the entire signal. To increase the angular resolution of the low frequency (LF) information and because only respiratory rates up to 1.5 Hz are of interest, each windowed waveform was down sampled to 3 Hz. Using the OPS technique, an AR model order of 20 was selected, and the calculated AR parameters were formulated as the transfer function of (2). FIG. 3 shows a Test signal corrupted with additive Gaussian white noise (AGWN) for SNR (a) −5 dB and (b) −10 dB. FIG. 3 shows the estimation result based on the SNR of −5 and −10 dB for each of the 55 segments. Note that there is a lag in the results in FIG. 1 since the data analysis is based on 60 s segments. It is shown that as the SNR decreases, the probability that incorrect poles are associated with the highest magnitude increases. More specifically, the resultant pole angles and magnitudes at time 60 s for an SNR of −10 dB are given in Table I. The pole angle of 0.3997 Hz, which is closest to the true rate of 0.4 Hz, has the magnitude of 0.9852. On the other hand, the pole angle of 0.6070 Hz has the magnitude of 0.9887, and consequently, is chosen as the respiratory rate since it has the largest magnitude among all chosen poles. Thus, with this choice, there is an error of 0.2 Hz deviation from the true respiratory rate.

B. Development of a Framework for Respiratory Rates in the Presence of Noise

A method for respiratory extraction based on PF combined with the OPS technique is presented below. A true PPG waveform from time $n-n_{seg}$ to time n is denoted by $S_{n-nseg:nn}$, (e.g., $n_{seg}$ represents a waveform segment). Based on the waveform of $S_{n-nseg:nn}$, the respiratory state at time n is denoted as R(n). By using the OPS technique and the breathing rates' ROI, $K_{roi}$, pairs of pole angles and their magnitudes are obtained. The pairs of pole angles and magnitudes are represented by the measurement vector P(n).

$$P(n) = f_{ops}(S_{n-nseg:n}, Q_1(n)) \qquad (10)$$

where $f_{ops}(\bullet)$ is a function of the OPS and the ROI, and $Q_1(n)$ is a noise term, which is not necessarily Gaussian. The measurement vector obtained by the OPS technique is represented by a $2K_{roi}$-dimensional parameter vector with the first $K_{roi}$ parameters representing $K_{roi}$-pole angles, and the last $K_{roi}$ parameters representing $K_{roi}$-pole magnitudes.

$$P(n) = [p_1^a p_2^a \ldots p_k^a \ldots p_{K_{roi}}^a p_1^m p_2^m \ldots p_k^m \ldots p_{K_{roi}}^m]^T \qquad (11)$$

where $p^a_k$ and $p^m_k$ represent kth pole angle and magnitude, respectively.

The respiratory state is considered as a Markov process, which can be modeled by the state transition relation as $$R(n) = T(R(n-n_{sam}), Q_2(n)) \qquad (12)$$

where $T(\bullet)$ is a known, not necessarily linear function of the previous state at time sample $n-n_{sam}$ and $Q_2(n)$ is a noise term, which is not necessarily Gaussian.

$P=(1:n)=[P(1) \ldots P(n-n_{sam})P(n)]$ denotes the concatenation of all measurements up to time n. The aim is to recursively estimate the conditional probability density p(R(n)|P(1:n)), from which the respiratory rate can be obtained as the mean of the density function. In practice, the posterior probability density is not available. However, considering the posterior probability density at time $n-n_{sam}$ as available, the posterior probability density at time n can be found through the Chapman-Kolmogorov equation and Bayes' rule $$p(R(n)|P(1:n-n_{sam})) = \int p(R(n)|R(n-1))p(R(n-n_{sam})|P(1:n-n_{sam}))dR(n-n_{sam}) \qquad (13)$$

$$p(R(n)|P(1:n)) \propto p(P(n)|R(n))p(R(n)|P(1:n-n_{sam})) \qquad (14)$$

where $p(R(n)|P(1:n-n_{sam}))$ is the posterior probability density, $p(R(n)|R(n-n_{sam}))$ is the state transition density, $p(R(n)|P(1:n))$ is the prediction probability density, and $p(P(n)|R(n))$ is the likelihood.

In general, no closed-form solution exists for (13) and (14) except in the special case, where $f_{ops}(\bullet)$ and $T(\bullet)$ in (10) and (12) are linear functions, and the noises $Q_1(n)$ and $Q_2(n)$ are Gaussian. In this case, the Kalman filter is the optimal solution. However, the pole angles obtained from the OPS method as well as Burg's method were found to have a non-Gaussian distribution. Hence, a PF approach is used, which is suitable for non-Gaussian problems, and approximate (13) and (14) via Monte Carlo simulations involving a set of particles. It has been shown that as the number of particles becomes large, their particle weights tend to approach the true distribution of the signal. Details concerning the generic PF algorithm are described in Arulampalam et al. With the framework outlined mentioned earlier, the algorithm for respiratory rate extraction using PF is described in FIG. 4.

Particle Generation

The first step to particle generation is to represent a prior probability density function $p(R(n)|P(1:n-n_{sam}))$ by a set of particles. Given the particles corresponding to the posterior probability density function of $p(R(n \; n_{sam})|P(1:n-nsam))$ obtained at time $n-n_{sam}$, new particles are generated at time n as $$R^i(n) = F(\bar{R}^i(n-n_{sam})) + Q_2(n) \qquad (9)(15)$$

where $R^i(n)$ are the ith generated particles, $i = \{1, 2, \ldots, I\}$ for the number of particles I, and $Q_2(n)$ is a Gaussian noise with N (0, $\sigma^2_{gen}$). In addition, R(n) is considered as a stationary process denoted as $$F(R(n-n_{sam})) = R(n-n_{sam}). \qquad (16)$$

Note that $\bar{R}^i(n-n_{sam})$ represents resampled particles obtained at time $n-n_{sam}$, and the resampling process will be explained in the proceeding section.

Weight Evaluation with Proposed Likelihood Functions

After the new particles corresponding to the prior probability density function $p(R(n)|P(1:n-n_{sam}))$ are generated, each particle weight should be evaluated based on the measurement vector P(n). The weighted particles represent the posterior probability density function of $p(R(n)|P(1:n))$. For the particle weight evaluation, several likelihood functions are considered. The likelihood functions should be chosen to reflect the fact that the respiratory rate is chosen as the pole angle with the highest pole magnitude. They should also reflect the fact that the pole angle with the highest pole magnitude is occasionally an incorrect respiratory rate especially with a low SNR, as shown in our simulation example. In this study, five different likelihood functions are considered: the strongest neighbor (SN) likelihood, the nearest neighbor (NN) likelihood, the weighted nearest neighbor (WNN) likelihood, the probability data association (PDA) likelihood, and the weighted probability data association (WPDA) likelihood.

SN Likelihood: The SN likelihood used herein is based on SN filtering (see X. R. Li, "Tracking in clutter with strongest neighbor measurements-Part I: Theoretical analysis," IEEE Trans. Autom. Control, vol. 43, no. 11, pp. 1560-1578, November 1998, incorporated by reference herein in its entirety and for all purposes). In SN filtering, the measurement with the highest intensity among the validated measurements is used and the others are discarded. Using the same concept, each particle weight is evaluated by the pole angle with the highest pole magnitude as $$w^i(n) = L_{SN}(p^c_{max} | R^i(n)) = \exp\left(-\frac{(R^i(n) - p^a_{max})^2}{2\sigma^2_{gau}}\right) \qquad (17)$$

where $L_{SN}(\bullet)$ is the SN likelihood operator for a particle weight evaluation, $i = \{1, 2, \ldots I\}$, and $p^a_{max}$ is the pole angle with the highest pole magnitude among the $K_{roi}$ pole angles.

NN and WNN Likelihood: The idea of the NN likelihood developed in these teachings is based on NN filtering (see A. Jadbabaie, J. Lin, and S. A. Morse, "Coordination of groups of mobile autonomous agents using nearest neighbor rules," IEEE Trans. Autom. Control, vol. 48, no. 6, pp. 988-1001, June 2003, incorporated by reference herein in its entirety and for all purposes). In NN filtering, the measurement closest to the predicted one is used, and the others are discarded. With the same concept, each particle weight is evaluated by its own nearest pole angle as $$w^j(n) = L_{NN}(p^a_{nn(i)} | R^i(n)) = \exp\left(-\frac{(R^i(n) - p^a_{nn(i)})^2}{2\sigma^2_{gau}}\right) \qquad (18\text{-}1)$$

where $L_{NN}(\bullet)$ is the NN likelihood operator for a particle weight evaluation, $i = \{1, 2, \ldots I\}$, and $p^a_{nn(i)}$ is the pole angle closest to each particle of $R^i(n)$.

The WNN likelihood extends the NN likelihood concept by weighting each pole angle's magnitude as $$w^j(n) = L_{WNN}(p^a_{nn(i)} | R^i(n)) \quad (18\text{-}2)$$

$$= \exp\left(-\frac{(R^i(n) - p^a_{nn(i)})^2}{2\sigma^2_{gau}}\right)$$

$$\frac{\exp\left(-\frac{(p^m_{nn(i)} - p^a_{max})^2}{2\sigma^2_w}\right)}{\sum_{m=1}^{K_{roi}} \exp\left(-\frac{(p^m_{nn(i)} - p^a_{max})^2}{2\sigma^2_w}\right)}$$

where $L_{WNN}(\bullet)$ is the WNN likelihood operator for a particle weight evaluation, $i=\{1, 2, \ldots I\}$, and $p^m_{nn(i)}$ is the pole magnitude corresponding to the pole angle $p^a_{nn(i)}$.

PDA and WPDA Likelihood: The idea of the PDA likelihood developed in these teachings is based on PDA filtering (see C. Rasmussen and G. D. Hager, "Probabilistic data association methods for tracking complex visual objects," IEEE Trans. Pattern Anal. Mach. Intell., vol. 23, no. 6, pp. 560-576, June 2001, incorporated by reference herein in its entirety and for all purposes). The PDA uses all of the data with different weights. For example, each particle weight is evaluated by all pole angles instead of using only one pole angle, defined as $$w^{j,k}(n) = L_{PDA}(P(n) | R^i(n)) = \exp\left(-\frac{(R^i(n) - p^a_k)^2}{2\sigma^2_{gau}}\right) \quad (19\text{-}1)$$

where $L_{PDA}(\bullet)$ is the PDA likelihood operator for particle weight evaluation, $i=\{1, 2 \ldots I\}$, $k=\{1, 2 \ldots K_{roi}\}$. Based on this configuration $I \times K_{roi}$ particle weights are evaluated. Note that each particle has multiple weights from which multiple posterior probability density functions can be obtained. Accordingly, we denote these particles by $R^{i,k}(n)$, where $i=\{1, 2, \ldots I\}$ and $k=\{1, 2, \ldots K_{roi}\}$.

Similar to WNN likelihood, the WPDA likelihood function extends the PDA likelihood concept by weighting each pole angle's magnitude as the following:

$$w^{j,k}(n) = L_{WPDA}(P(n) | R^i(n)) \quad (19\text{-}2)$$

$$= \exp\left(-\frac{(R^i(n) - p^a_k)^2}{2\sigma^2_{gau}}\right) \times$$

$$\frac{\exp(-(p^m_k - p^a_{max})^2 / 2\sigma^2_w)}{\sum_{m=1}^{K_{roi}} \exp(-(p^m_k - p^a_{max})^2 / 2\sigma^2_w)}$$

where $L_{WPDA}(\bullet)$ is the WPDA likelihood operator for a particle weight evaluation, $i=\{1, 2, \ldots I\}$ and $k=\{1, 2, \ldots K_{res}\}$.

Weight Normalization and Resampling: For respiratory rate calculation, the particle weights are normalized as $$\overline{w}^i(n) = \frac{w^i(n)}{\sum_{i=1}^{I} w^i(n)} \text{ for } SN, NN, \text{ and } WNN \quad (20\text{-}1)$$

and $$\overline{w}^{j,k}(n) = \frac{w^{j,k}(n)}{\sum_{k=1}^{K}\left(\sum_{i=1}^{I} w^{j,k}(n)\right)} \text{ for } PDA \text{ and } WPDA. \quad (20\text{-}2)$$

After particle weight normalization, the mean of the particles' posterior probability density is calculated for the respiratory rate extraction. Once the mean of the particles' posterior probability density has been calculated, the particles are resampled to generate new particles at the next time instant, $n+n_{sam}$. The basic idea of resampling is to eliminate particles that have small weights and to concentrate on particles with large weights. In addition, the resampling process reduces the degeneracy problem, where after a few iterations, all but one particle will have negligible weight. As noted in the previous section, the resampled particles are denoted by $\overline{R}^i(n)$. Once the particles have been normalized, the resampled particles are generated using the scheme depicted in FIG. 5. FIGS. 5A-5B are Ilustrations of resampling processes. The sizes of the circles in FIGS. 5(a), 5(b) represent the value of each particle weight. In FIG. 5(a), the I to I resampling process is illustrated for the SN-, NN-, and WNN likelihoods In FIG. 5(b), the $I \times K_{roi}$ to I resampling process is illustrated for the PDA- and WPDA likelihoods.

E. PPG Data Collection on Human Subjects

1) Simulation Procedures: To evaluate the proposed PF algorithms for respiratory rate estimation, simulations using the test signal were performed with additive GWN (AGWN) so that the SNR was −20 dB. The respiratory rate estimation performance was compared among six methods: SN-PF, NN-PF, WNN-PF, PDA-PF, WPDA-PF, and OPS only. 100 particles were used for all realizations including comparison to both experimental and simulated data. For an initial set of particles, the pole angle with the highest magnitude in the beginning of the time sample was chosen. For quantitative comparison of all methods, a root mean square error (RMSE) $E(n)$ between $\hat{R}(n)$ and $R(n)$ was computed, where $\hat{R}(n)$ and $R(n)$ represent an estimated and a true respiratory rate of the wave-form segment at time n, respectively. For every realization, 55 $\hat{R}(n)$ were estimated (i.e., n={60, 70, ..., 600}). In addition, a deviation percentage was used. The deviation percentage denotes how many of the estimated respiratory rates deviate more than $Th_{dev}$ from a true rate. The deviation was counted as $$|\hat{R}(n) - R(n)| > Th_{dev}. \quad (21)$$

In the simulation result, $Th_{dev}$ was set to 0.2, 0.3, and 0.4 Hz. In addition, the initial model order for the OPS was set to 30. The breathing rate of interest was set to $f_{low}=0.15$ Hz and $f_{high}=0.9$ Hz. An important issue in PF design is the choice of the variance of the particle sampling density (particle distribution). Thus, the values of $\sigma^2_{gen}$, $\sigma^2_{gau}$ and $\sigma^2_w$ play important roles in determining estimation accuracy. The value of $\sigma^2_{gen}$ represents the variance of generated particles as described in Wang et al., and the chosen value predefines the range of the predicted respiratory rate. A selected value of $\sigma^2_{gen}$ should not deviate too much from the selected chosen pole magnitude via the OPS. The values of $\sigma^2_{gau}$ and $\sigma^2_w$ represent the variances of likelihood functions as described in Zou et al., Lee et al. and Zou et al. Specifically, a choice of $\sigma^2_{gau}$ determines the spread of pole angles each particle weight is evaluated, and likewise for the choice of $\sigma^2_w$ for the likelihood functions of WNN-PF and WPDA-PF. For NN-PF and PDA-PF, $\sigma^2_w$=(infinity) in (18-

2) and (19-2), which results in (18-1) and (19-1), respectively. For other likelihood functions, the PF parameters were set to $\sigma^2_{gen}=0.01$, $\sigma^2_{gau}=0.0001$, and $\sigma^2_w=0.0025$.

2) PPG Data Collection on Human Subjects: For the PPG waveform acquisition, an MP506 pulse oximeter (Nellcor Oximax, Boulder, Colo.) reusable sensor (Durasensor DS-100 A) was used, which incorporates a conditioning circuit and has an analog output of 4.864 kHz. The PPG waveforms were collected on 15 healthy subjects with metronome respiratory rates ranging from healthy subjects instructed to breathe at the rates of 0.7 and 0.8 Hz. Finally, ten additional healthy subjects were recruited and they were instructed to breathe at the rates of 1.0, 1.2, and 1.5 Hz. We categorized the respiratory rates of 0.2 and 0.3 Hz as the LF, the rates of 0.4-0.6 Hz as the high frequency (BF), the rates of 0.7 and 0.8 Hz as the ultra-BF (UHF), and the rates of 1.0-1.5 Hz as the extremely BF (EHF). Among the 15 healthy subjects, seven females and eight males of age 21.0±1.2 years were involved, in the eight healthy subjects (for UHF experiment), one female and seven males of age 28.4±3.6 years participated, and in the ten healthy subjects (for EHF experiment), three females and seven males of age 26.7±4.6 years participated. None of the subjects had cardiorespiratory or related pathologies.

The PPG data were collected in the supine and upright positions for subjects instructed to breathe in the LF, BF, and UHF ranges. For subjects in the EHF protocol, the PPG data were collected only in the upright position because many participants had trouble breathing at these high rates in the supine position. The pulse oximeter sensor was attached to the subjects' left index or middle finger. The subjects were instructed to breathe at a constant rate according to a timed beeping sound so that the subjects inhaled and exhaled when the beeping sound was heard. Three minutes of PPG data were collected for each position for the breathing rates consisting of LF, BF, and UHF. For EHF rates, only 1-2 min of PPG signals were collected because most subjects could not keep up with extremely high breathing rates. We also simultaneously measured respiration signals using the respitrace system, which uses inductive plethysmography to provide calibrated voltage outputs corresponding to rib cage and abdominal compartment volume changes. From the respitrace system, true respiratory rates were evaluated by counting the number of peaks in a given minute. For those subjects breathing at the EHF rates, we also measured their ECG signals.

For all signals, consisting of PPG, respiration, and ECG signals, we used the PowerLab/4sp (ADInstrument, Inc.) for data acquisition. The PowerLab/4sp was connected to a laptop via universal serial bus, and the Chart v4.2.2 software was used to sample the analog signal at 400 Hz for EHF data and 200 Hz for LF, BF, and UHF data. All PPG data were low-pass filtered to 10 Hz. We performed the respiratory rate estimation on 60 s segments for the LF, BF, and UHF data, while 30-s segment data were used for the EHF data. All data segments were shifted by 10 s for the entire PPG waveform recording. The initial model order was set to 30 for the OPS. The breathing rate of interest was set to $f_{low}=0.15$ Hz and $f_{high}=0.9$ Hz for LF, BE, and UHF data. For the EHF data, we set the breathing rate of interest to $f_{low}=0.15$ Hz and $f_b < f_{high} < f_h$. Furthermore, in order to investigate the effect on the heart signal (fh), an additional ROI was set as $f_{low}=0.15$ Hz and $f_b < f_h < f_{high}$. The PF parameters were set to $\sigma^2_{gen}=0.01$, $\sigma^2_{gau}=0.0001$, and $\sigma^2_w=0.0025$, which are the same as in the simulation example.

Results

A. Simulation Results

FIG. 6 shows the results of respiratory rate estimation by the OPS only (without the PF) and five different PF methods consisting of SN-PF, NN-PF, WNN-PF, PDA-PF, and WPDAPF with the test signal as described above. It summarizes the breathing frequency of 0.4 Hz based on 100 realizations for each method, which resulted in the estimation of 5500 respiratory rates. In the results shown in FIGS. 6(a)-6(b), the number of particles used was 100. FIG. 6(a) shows the deviation percentages defined in X. Xiao, Y. Li, and R. Mukkamala, "A model order selection criterion with applications to cardio-respiratory-renal systems," *IEEE Trans. Biomed. Eng.*, vol. 52, no. 3, pp. 445-453, March 2005, which is incorporated by reference herein in its entirety for all purposes. Deviation percentage are reported as a function of three different $Th_{dev}$ values: 0.2, 0.3, and 0.4. Regardless of the chosen threshold value, both PDA-PF and WPDA-PF showed the smallest deviation percentage, while the OPS had the largest. FIG. 6(b) shows the mean of RMSE and its mean plus two standard deviations. All PF methods showed smaller RMSE values than OPS only. The asterisks indicate the significant difference (p<0.01) between OPS only and each of the five different likelihood functions. Among the PF methods, there was no significant difference. FIG. 7(a)-(c) summarizes the mean and standard deviation of the RMSEs and the computation time as the number of particles varied from 1 to 200. FIG. 7(a) shows the Mean of RMSEs. FIG. 7(b) shows the Standard deviation of RMSEs. FIG. 7(c) shows the Computational time (programs running on MATLAB R2007b). These results suggest that approximately only 25 particles are needed to obtain reasonably accurate results for all proposed PF methods. There was a significant increase in the computation time with both PDA-PF and WPDA-PF when the number of particles was higher than 75.

B. Experimental Data Results

1) Result of LF, HF, and UHF Respiratory Rate: FIGS. 8 and 9 show the RMSEs for each method for LF (0.2-0.3 Hz), HF(0.4-0.6 Hz), and UHF (0.7-0.8 Hz) during the supine and upright positions, respectively. The circles (red) above and below each method represent the 95th and the 5th percentiles of all estimation results for every subject, respectively. Whiskers (blue) above and below represent the 90th and the 10th percentiles, respectively. The bars above, middle, and below represent the 75th, the 50th, and the 25th percentiles, respectively. In addition, the asterisks indicate the mean value. Tables II and III summarize the measures of accuracy by tabulating the mean and variance of RMSE across all subjects for both supine and upright positions. For the statistical analysis, t-test (p<0.01) was used among the six methods.

In the supine position, as shown in FIG. 8 and Table H, the mean of RMSE with WNN-PF was the lowest followed by NNPF, WPDA-PF, PDA-PF, SN-PF, and OPS only for the LF respiratory rates. Similarly, the variances of RMSE with NN-PF, WNN-PF, and PDA-PF were the lowest followed by WPDAPF, SN-PF, and OPS only. For the BF respiratory rates, the mean of RMSE with NN-PF was the lowest followed by WNNPF, PDA-PF, WPDA-PF, SN-PF, and OPS only. The variance of RMSE with PDA-PF was the lowest followed by NN-PF, WNN-PF, WPDA-PF, SN-PF, and OPS only. For the UHF, the mean of RMSE with PDA-PF was the lowest followed by NNPF, WNNA-PF, WPDA-PF, SN-PF, and OPS only. Similarly, the variance of RMSE with PDA-PF was the lowest followed by WPDA-PF, WNN-PF, NN-PF, SN-PF, and OPS only. Based on the RMSE distribution, all five proposed PF methods showed significantly lower RMSEs than OPS only in both LF and BF respiratory rates.

In the UHF respiratory rate range, the four PF methods NN-PF, WNN-PF, PDA-PF, and WPDA-PF all showed significantly lower RMSE than OPS only. Among the PF methods, in the LF respiratory rates, NN-PF, WNN-PF, and PDA-PF showed significantly lower RMSE than SN-PR Also, NN-PF and WNN-PF showed significantly lower RMSE than WPDAPF. There was no significant difference between NN-PF and WNN-PE In the BF respiratory rates, NN-PF, WNN-PF, PDAPF, and WPDA-PF showed significantly lower RMSE than SNPE There was no significant the supine position. Thus, regardless of subject positions, NNPF and WNN-PF showed significantly lowest RMSE than any other method for the LF respiratory rate. For the BF respiratory rate, NN-PF, WNN-PF, PDA-PF, and WPDA-PF showed significantly lowest RMSE than any other method. For the UHF respiratory rate, all proposed methods showed significantly lowest RMSE. As shown in FIG. 7(c), PDA-PF and WPDA-PF requires much more computation time than NN-PF and WNN-PF, it is concluded that NN-PF and WNN-PF achieved the best result for LF, BF, and UHF respiratory rates.

TABLE II

MEANS AND VARIANCES OF RMSES AND CORRESPONDING STATISTICAL SIGNIFICANCE WITH P-VALUES OF SIX METHODS IN RESPIRATORY RANGES LF (0.2-0.3 HZ), HF (0.4-0.6 HZ), AND UHF (0.7-0.8 HZ) FOR SUPINE POSITION: MEANS AND VARIANCES OF RMSES

| | | OPS only | | SN-PF | | NN-PF | | WNN-PF | | PDA-PF | | WPDA-PF | |
|---|---|---|---|---|---|---|---|---|---|---|---|---|---|
| Position | True Rate (Hz) | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (Hz) | Variance of RMSE (Hz) |
| Supine | LF (0.2-0.3) | 0.1688 | 0.0593 | 0.1167 | 0.0270 | 0.0446 | 0.0061 | 0.0390 | 0.0063 | 0.0910 | 0.0061 | 0.0675 | 0.0248 |
| | HF (0.4-0.6) | 0.1356 | 0.0211 | 0.0997 | 0.0118 | 0.0394 | 0.0030 | 0.0450 | 0.0038 | 0.0512 | 0.0024 | 0.0646 | 0.0078 |
| | UHF (0.7-0.8) | 0.2160 | 0.0442 | 0.1666 | 0.0267 | 0.1257 | 0.0267 | 0.1278 | 0.0267 | 0.1104 | 0.0212 | 0.1386 | 0.0248 |

TABLE III

MEANS AND VARIANCES OF RMSES AND CORRESPONDING STATISTICAL SIGNIFICANCE WITH P-VALUES OF SIX METHODS IN RESPIRATORY RANGES LF (0.2-0.3 HZ), HF (0.4-0.6 HZ), AND UHF (0.7-0.8 HZ) FOR UPRIGHT POSITION: MEANS AND VARIANCES OF RMSES

| | | OPS only | | SN-PF | | NN-PF | | WNN-PF | | PDA-PF | | WPDA-PF | |
|---|---|---|---|---|---|---|---|---|---|---|---|---|---|
| Position | True Rate (Hz) | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (HZ) | Variance of RMSE (Hz) | Mean of RMSE (Hz) | Variance of RMSE (Hz) |
| Upright | LF (0.2-0.3) | 0.1207 | 0.0371 | 0.0692 | 0.0113 | 0.0324 | 0.0040 | 0.0326 | 0.0052 | 0.0698 | 0.0037 | 0.0332 | 0.0043 |
| | HF (0.4-0.6) | 0.0654 | 0.0106 | 0.0461 | 0.0075 | 0.0232 | 0.0036 | 0.0230 | 0.0045 | 0.0305 | 0.0023 | 0.0273 | 0.0050 |
| | UHF (0.7-0.8) | 0.0633 | 0.0250 | 0.0301 | 0.0056 | 0.0348 | 0.0022 | 0.0214 | 0.0020 | 0.0413 | 0.0017 | 0.0103 | 0.0051 | difference among the four methods. In the UHF respiratory rates, there was no significantly difference among the PF methods.

In the upright position, as shown in FIG. 9 and Table III, the means of RMSE with NN-PF, WNN-PF, and WPDA-PF were the lowest followed by PDA-PF, SN-PF, and OPS for the LF respiratory rates. The variance of RMSE with PDA-PF was the lowest followed by NN-PF, WPDA-PF, PDA-PF, SN-PF, and OPS. For the BF respiratory rates, the means of RMSE with NN-PF, WNN-PF, and WPDA-PF were the lowest followed by PDA-PF, SN-PF, and OPS. The variance of RMSE with PDA-PF was the lowest followed by NN-PF, WNN-PF, WPDA-PF, SN PF, and OPS. For the UHF, the mean of RMSE with WPDA-PF was the lowest followed by WNN-PF, SN-PF, NN-PF, PDA-PF, and OPS. The variance of RMSE with PDA-PF was the lowest followed by WNN-PF, NN-PF, WPDA-PF, SN-PF, and OPS. Based on the RMSE distribution, all five proposed PF methods showed significantly lower RMSE than OPS only in all respiratory ranges of LF, BF, and UHF. In addition, among the PF methods, the same significant differences were observed in 2) Result of EHF Respiratory Rate: FIG. 10(a) shows the RMSE for each method for EHF (1.0-1.5 Hz) breathing rates during the upright position. For these EHF rates, the breathing frequency ($f_b$) may possibly overlap with a heart rate frequency ($f_h$), thus the range of interest is set from $f_{low}$=0.15 Hz to $f_b < f_{high} < f_h$. For example, when the heart rate is 1.6 Hz and the respiratory rate is 1.2 Hz, $f_{high}$ was set to 1.4 Hz. As shown in FIG. 8(a) and Table IV (first row), the mean value of RMSE with WNN-PF was the lowest followed by NN-PF, WPDA-PF, PDA-PF, SN-PF, and OPS. For the variance of RMSE values, PDA-PF, NN-PF, and WNN-PF were the lowest followed by WPDA-PF, SN-PF, and OPS. The five likelihood functions showed significantly lower RMSE than OPS. Based on the RMSE distribution, all five PF methods showed significantly lower RMSE than OPS only. Among the PF methods, there was no significant difference. FIG. 10(b) shows the RMSE for each method for EHF (1.0-1.5 Hz) when $f_b < f_h < f_{high}$ (the range of interest contains heart rate as well as respiratory rate). In this case, it was observed that heart rate and respiratory rate were correctly detected approximately at only 60% and 40%, respectively, by the OPS technique. As shown in FIG. 10(b) and Table IV (second row), the respiratory rate extraction became inaccurate due to the heart rate detection. Consequently, there was no significant difference among all methods. Thus, for the respiratory rate extraction in the EHF range, it should be ensured that the heart and respiratory rates do not overlap. Otherwise, in most instances, the heart rate will be selected as the dominant pole instead of the respiratory frequency.

61/392,271, and J. Lee, and K. Chon, "Time-Varying Autoregressive Model-Based Multiple Model Particle Filtering Algorithm for Respiratory Rate Extraction from Pulse Oximeter," IEEE Trans. BME, which is also provided as Appendix III in U.S. Provisional Application Ser. No. 61/392,271, all of which are incorporated by reference herein in their entirety for all purposes.

We presented the combined OPS-PF algorithm and examined the robustness of five different likelihood functions for

TABLE IV

MEANS AND VARIANCES OF RMSES AND CORRESPONDING STATISTICAL SIGNIFICANCE WITH P-VALUES OF SIX METHODS IN RESPIRATORY RANGE OF EHF (1.0-1.5 HZ) FOR UPRIGHT POSITION: MEANS AND VARIANCES OF RMSES

| | OPS only | | SN-PF | | NN-PF | | WNN-PF | | PDA-PF | | WPDA-PF | |
|---|---|---|---|---|---|---|---|---|---|---|---|---|
| | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (Hz) | Variance of RMSE (Hz) | Mean of RMSE (Hz) | Variance of RMSE (Hz) |
| $f_b < f_{high} < f_h$ | 0.1688 | 0.0593 | 0.1167 | 0.0270 | 0.04457 | 0.0061 | 0.0390 | 0.0063 | 0.0910 | 0.0061 | 0.0675 | 0.0248 |
| $f_b < f_h < f_{high}$ | 0.1356 | 0.0211 | 0.0997 | 0.0118 | 0.0394 | 0.0030 | 0.0450 | 0.0038 | 0.0512 | 0.0024 | 0.0646 | 0.0078 |

Effect of initial set of particles: The performances of PF methods are affected by the initial set of particles chosen. In the results for the above exemplary embodiments, the initial set of particles was chosen based on the pole angle with the highest magnitude as determined by OPS. The accuracy of the PF method will certainly benefit and converge faster to a true solution if the initially chosen set of particles is closest to the true respiratory rate. This is a reason why in the above presented exemplary embodiments the OPS is combined with PF to obtain near-optimal solutions Multiple dynamic model: In the above presented exemplary embodiments, only fixing the breathing rate for the entire duration of the data recording was considered. In the event of different breathing rates in a sample, the method of the above presented exemplary embodiments would not be optimal. For example, a subject might breathe at one rate and then either slowly or abruptly transition to a different breathing rate. To account for these different scenarios, a dynamic model can be used. For example, in the case of a constant breathing rate followed by an increase and then decrease in breathing rates, the following three models may be considered:

$$R^{i,j}(n) = F_j(\overline{R}^i(n-n_{sam})) + Q_2(n), \text{for } j=1,2,3 \quad (22)$$

where $$F_1(R(n-n_{sam})) = R(n-n_{sam}) \quad (23\text{-}1)$$

$$F_2(R(n-n_{sam})) = R(n-n_{sam}) + I_R \quad (23\text{-}2)$$

$$F_3(R(n-n_{sam})) = R(n-n_{sam}) - D_R \quad (23\text{-}3)$$

where $I_R$ is the increased rate and $D_R$ is the decreased rate. Note that 3×I predicted particles will be generated for these particular models. Elucidation of the above described embodiments can be found in J. Lee, and K. H. Chon, "Respiratory Rate Extraction Via an Autoregressive Model Using the Optimal Parameter Search Criterion," Ann Biomed Eng, May 25, which is al so provided as Appendix I in U.S. Provisional Application Ser. No. 61/392,271, J. Lee, and K. H. Chon, "An Autoregressive Model-Based Particle Filtering Algorithms for Extraction of Respiratory Rates as High as 90 Breaths per Minute from Pulse Oximeter," IEEE Trans Biomed Eng, which is also provided as Appendix II in U.S. Provisional Application Ser. No.

estimation of respiratory rates directly from pulse oximeter recordings. They were evaluated on 33 healthy subjects with a wide range of breathing rates varying from 0.2-1.5 Hz. It was found that the combined OPS-PF approaches provided better accuracy than the solely OPS-based AR model for all breathing rates considered. The robustness of the combined OPS-PF approaches is evident as the accuracy is intact even for breathing rates as high as 1.5 Hz. This indicates that the method of these teachings is also applicable for extracting breathing rates during exercise. It should also be noted that the processing time was 10 ms for SN-PF, NN-PF, and WNN-PF, and 30 ms for PDA-PF and WPDA-PR Thus the combined OPS-PF approach can be realizable in real time for practical applications.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Elements and components described herein may be further divided into additional components or joined together to form fewer components for performing the same functions.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, any physical medium with patterns of holes, a RAM, a PROM, and EPROM, a FLASH-EPROM, any other memory chip or cartridge, all of which are non-transitory. As stated in the USPTO 2005 Interim Guidelines for Examination of Patent Applications for Patent Subject Matter Eligibility, 1300 Off. Gaz. Pat. Office 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

Although the teachings have been described with respect to various embodiments, it should be realized these teachings are also capable of a wide variety of further and other embodiments within the spirit and scope of the appended claims.

What is claimed is:

1. A method for detecting respiratory rate of a patient from pulse oximeter data, the method comprising the steps of:
   receiving a photoplethysmography (PPG) signal obtained from the patient;
   obtaining, from an autoregressive (AR) representation of the photoplethysmography (PPG) signal obtained from the patient, the respiratory rate of the patient using an iterative Particle Filtering Monte Carlo method, where the respiratory state is considered a Markov process, modeled by the state transition relation; where a distribution of respiratory rate is the distribution approximated by Monte Carlo sampling, measurements are magnitudes and phase of poles for a frequency transfer function of the AR representation, a phase angle of one pole being given by $2\pi$ times a sampling interval times a frequency, the magnitudes and phase of the poles obtained by:
      obtaining parameters for the AR representation using a projection onto linearly independent non-orthogonal bases;
      obtaining poles for a frequency transfer function of the AR representation;
   representing pairs of pole angles and magnitudes by a measurement vector that is a function of a frequency region of interest and a noise component;
   the respiratory rate being determined by a weighed sum of particles from the Particle Filtering Monte Carlo method;
   wherein a processor executes the step for obtaining the respiratory rate.

2. The method of claim 1 wherein the iterative Particle Filtering Monte Carlo method comprises:
   a. selecting an initial group of particles, each particle from said initial group being a different value for the respiratory rate; each particle from said initial group being assigned a weight equal to an inverse of a number of particles from said initial group;
   b. obtaining a new group of particles by propagating the initial group of particles;
   c. obtaining the measurements; the measurements being the magnitudes and the phase of the poles for the frequency transfer function of the AR representation obtained by:
      obtaining the parameters for the AR representation using the projection onto linearly independent non-orthogonal bases;
      obtaining the poles for the frequency transfer function of the AR representation;
   d. obtaining a new weight for each particle from said new group by using a predetermined likelihood function;
   e. selecting a candidate respiratory rate of a patient equal to a weighted sum of the particles in the new group of particles; and
   f. resampling the new group of particles.

3. The method of claim 2 wherein the predetermined likelihood function is a strongest neighbor (SN) likelihood function.

4. The method of claim 2 wherein the predetermined likelihood function is a nearest neighbor (NN) likelihood function.

5. The method of claim 2 wherein the predetermined likelihood function is a weighted nearest neighbor (WNN) likelihood function.

6. The method of claim 2 wherein the predetermined likelihood function is a probabilistic data association (PDA) likelihood function.

7. The method of claim 2 wherein the predetermined likelihood function is a weighted probabilistic data association (WPDA) likelihood function.

8. The method of claim 1 wherein a frequency region of interest is between about 0.15 Hz and about 1.5 Hz.

9. A system comprising:
   at least one processor; said at least one processor receiving a photoplethysmography (PPG) signal obtained from the patient, and
   a computer usable memory having computer readable code embodied therein, the computer readable code causing said at least one processor to:
      obtain, from an autoregressive (AR) representation of the photoplethysmography (PPG) signal obtained from the patient, a respiratory rate of the patient using an iterative Particle Filtering Monte Carlo method, where the respiratory state is considered a Markov process, modeled by the state transition relation; where a distribution of respiratory rate is the distribution approximated by Monte Carlo sampling, measurements are magnitudes and phase of poles for a frequency transfer function of the AR representation, a phase angle of one pole being given by $2\pi$ times a sampling interval times a frequency, the magnitudes and phase of the poles obtained by:
         obtaining parameters for the AR representation using a projection onto linearly independent non-orthogonal bases;
         obtaining the poles for a frequency transfer function of the AR representation;
      represent pairs of pole angles and magnitudes by a measurement vector that is a function of a frequency region of interest and a noise component;
      the respiratory rate being determined by a weighed sum of particles from the Particle Filtering Monte Carlo method.

10. The system of claim 9 wherein the iterative Particle Filtering Monte Carlo method comprises:
   a. selecting an initial group of particles, each particle from said initial group being a different value for the respiratory rate; each particle from said initial group being assigned a weight equal to an inverse of a number of particles from said initial group;
   b. obtaining a new group of particles by propagating the initial group of particles;
   c. obtaining the measurements; the measurements being the magnitudes and the phase of the poles for the frequency transfer function of the AR representation obtained by:

obtaining the parameters for the AR representation using the projection onto linearly independent non-orthogonal bases;

obtaining the poles for the frequency transfer function of the AR representation;

d. obtaining a new weight for each particle from said new group by using a predetermined likelihood function;

e. selecting a candidate respiratory rate of a patient equal to a weighted sum of the particles in the new group of particles; and f. resampling the new group of particles.

11. The system of claim 10 wherein the predetermined likelihood function is a strongest neighbor (SN) likelihood function.

12. The system of claim 10 wherein the predetermined likelihood function is a nearest neighbor (NN) likelihood function.

13. The system of claim 10 wherein the predetermined likelihood function is a weighted nearest neighbor (WNN) likelihood function.

14. The system of claim 10 wherein the predetermined likelihood function is a probabilistic data association (PDA) likelihood function.

15. The system of claim 10 wherein the predetermined likelihood function is a weighted probabilistic data association (WPDA) likelihood function.

16. The system of claim 9 wherein a frequency region of interest is between about 0.15 Hz and about 1.5 Hz.

17. A computer program product comprising:
a non-transitory computer usable medium having computer readable code embodied therein for detecting respiratory rate of a patient, the computer readable code, when executed by at least one processor, causes the at least one processor to:
obtain parameters for an autoregressive (AR) representation of a photoplethysmography (PPG) signal obtained from the patient, the parameters being obtained using a projection onto linearly independent non-orthogonal bases;
obtain poles for a frequency transfer function of the AR representation; and
select a pole with a highest magnitude in a frequency region of interest; the respiratory rate being determined by an angle of the pole with the highest magnitude divided by $2\pi$ times a sampling interval; wherein the respiratory rate is obtained from the pulse oximeter data.

18. The computer program product of claim 17 wherein the computer readable code is also capable of causing said at least one processor to filter the PPG signal before obtaining parameters for the AR representation.

19. The computer program product of claim 18 wherein the computer readable code is also capable of causing said at least one processor to downsample the filtered PPG signal.

20. A computer program product comprising:
a non-transitory computer usable medium having computer readable code embodied therein for detecting respiratory rate of a patient, the computer readable code, when executed by at least one processor, causes the at least one processor to:
obtain, from an autoregressive (AR) representation of a photoplethysmography (PPG) signal obtained from the patient, the respiratory rate of the patient using an iterative Particle Filtering Monte Carlo method, where the respiratory state is considered a Markov process, modeled by the state transition relation; where a distribution of respiratory rate is the distribution approximated by Monte Carlo sampling, measurements are magnitudes and phase of poles for a frequency transfer function of the AR representation, a phase angle of one pole being given by $2\pi$ times a sampling interval times a frequency, the magnitudes and the phase of the poles obtained by:
obtaining parameters for the AR representation using a projection onto linearly independent non-orthogonal bases; and
obtaining the poles for a frequency transfer function of the AR representation;
represent pairs of pole angles and magnitudes by a measurement vector that is function of a frequency region of interest and a noise component;
the respiratory rate being determined by a weighed sum of particles from the Particle Filtering Monte Carlo method.

21. The computer program product of claim 20 wherein the iterative Particle Filtering Monte Carlo method comprises:

a. selecting an initial group of particles, each particle from said initial group being a different value for the respiratory rate; each particle from said initial group being assigned a weight equal to an inverse of a number of particles from said initial group;

b. obtaining a new group of particles by propagating the initial group of particles;

c. obtaining the measurements; the measurements being the magnitudes and the phase of the poles for the frequency transfer function of the AR representation obtained by:
obtaining parameters for the AR representation using the projection onto linearly independent non-orthogonal bases;
obtaining the poles for the frequency transfer function of the AR representation;

d. obtaining a new weight for each particle from said new group by using a predetermined likelihood function;

e. selecting a candidate respiratory rate of a patient equal to a weighted sum of the particles in the new group of particles; and f. resampling the new group of particles.

22. The computer program product of claim 21 wherein the predetermined likelihood function is a strongest neighbor (SN) likelihood function.

23. The computer program product of claim 21 wherein the predetermined likelihood function is a nearest neighbor (NN) likelihood function.

24. The computer program product of claim 21 wherein the predetermined likelihood function is a weighted nearest neighbor (WNN) likelihood function.

25. The computer program product of claim 21 wherein the predetermined likelihood function is a probabilistic data association (PDA) likelihood function.

26. The computer program product of claim 21 wherein the predetermined likelihood function is a weighted probabilistic data association (WPDA) likelihood function.

* * * * *